(12) United States Patent
Lim et al.

(10) Patent No.: US 12,139,725 B2
(45) Date of Patent: Nov. 12, 2024

(54) COMPOSITION FOR PROMOTING STEM CELL DIFFERENTIATION, COMPRISING PROGENITOR CELL CULTURE SOLUTION AND MULTILAYER GRAPHENE FILM, AND USE THEREOF

(71) Applicants: SEOUL NATIONAL UNIVERSITY R & DB FOUNDATION, Seoul (KR); BIOGRAPHENE INC., Suwon-si (KR)

(72) Inventors: Jeong Mook Lim, Seoul (KR); Ji Yeon Ahn, Seoul (KR); Jong Bo Park, Seoul (KR); Byung Hee Hong, Suwon-Si (KR); Woo Sub Yang, Seoul (KR)

(73) Assignees: SEOUL NATIONAL UNIVERSITY R&DB FOUNDATION, Seoul (KR); BIOGRAPHENE INC., Suwon-si (KR)

( * ) Notice: Subject to any disclaimer, the term of this patent is extended or adjusted under 35 U.S.C. 154(b) by 992 days.

(21) Appl. No.: 17/055,441

(22) PCT Filed: May 14, 2019

(86) PCT No.: PCT/KR2019/005765
§ 371 (c)(1),
(2) Date: Nov. 13, 2020

(87) PCT Pub. No.: WO2019/221477
PCT Pub. Date: Nov. 21, 2019

(65) Prior Publication Data
US 2021/0180018 A1    Jun. 17, 2021

(30) Foreign Application Priority Data
May 14, 2018    (KR) .................. 10-2018-0055015

(51) Int. Cl.
*C12N 5/077* (2010.01)
*A61K 35/32* (2015.01)
*C01B 32/186* (2017.01)

(52) U.S. Cl.
CPC ............ *C12N 5/0654* (2013.01); *A61K 35/32* (2013.01); *C01B 32/186* (2017.08); *C12N 2506/1384* (2013.01)

(58) Field of Classification Search
CPC .......... C12N 5/0654; C12N 2506/1384; A61K 35/32; C01B 32/186
See application file for complete search history.

(56) References Cited

U.S. PATENT DOCUMENTS

2012/0076830 A1   3/2012   Sitharaman et al.
2013/0095083 A1   4/2013   Oezyilmaz et al.

FOREIGN PATENT DOCUMENTS

KR   10-2014-0098714 A   8/2014
KR   10-2016-0016687 A   2/2016
KR   10-2018-0005130 A   1/2018

OTHER PUBLICATIONS

Barbero, A., et al., "Plasticity of clonal populations of dedifferentiated adult human articular chondrocytes," Arthritis Rheum 48(5):1315-1325. doi: 10.1002/art.10950. (Year: 2003).*
Duan, L., et al., "Cytokine networking of chondrocyte dedifferentiation in vitro and its implications for cell-based cartilage therapy," Am J Transl Res 7(2): 194-208 (Year: 2015).*
Shearer, C. J., et al., "Accurate thickness measurement of graphene," Nanotechnology 27(12): 125704. doi: 10.1088/0957-4484/27/12/125704. Epub Feb. 19, 2016. (Year: 2016).*
Fujioka-Kobayashi et al., "Bone conditioned media (BCM) improves osteoblast adhesion and differentiation on collagen barrier membranes", BMC Oral Health, 2017, vol. 17(1), pp. 1-7.
Hwang et al., "Enhanced Chondrogenesis by Three-dimensional Co-culture of Chondrocytes and Mesenchymal Stem Cells", Korean Society for Biotechnology and Bioengineering Journal, 2016, vol. 31(2), pp. 120-125.
Yoon et al., "The Use of Graphene for Regenerative Medicine", Korean Society for Biotechnology and Bioengineering Journal, vol. 27(5), pp. 273-280.
EESR dated Jan. 14, 2022 for the corresponding European Patent Application No. 19804512.2.
Akhavan et al., "Graphene nanogrids for selective and fast osteogenic differentiation of human mesenchymal stem cells", Carbon, 2013, vol. 59, pp. 200-211.
Deliormanh et al., "Biological Response of Osteoblastic and Chondrogenic Cells to Graphene-Containing PCL/Bioactive Glass Bilayered Scaffolds for Osteochondral Tissue Engineering Applications", Applied Biochemistry and Biotechnology, 2018, vol. 186, No. 4, pp. 972-989.
Hwang et al., "In vivo commitment and functional tissue regeneration using human embryonic stem cell-derived mesenchymal cells", PNAS, 2008, vol. 105, No. 52, pp. 20641-20646.
Kim et al., "Synergistic effects of nanotopography and co-culture with endothelial cells on osteogenesis of mesenchymal stem cells", Biomaterials, 2013, vol. 34, No. 30, pp. 7257-7268.
Kim et al., "Bioactive effects of graphene oxide cell culture substratum on structure and function of human adipose-derived stem cells : Graphene Oxide for Modulating Structure and Function of hASCs", J Biomed Mater Res Part A, 2013, vol. 101, No. 12, pp. 3520-3530.
Kim, "Enhanced osteogenic commitment of mesenchymal stem cells on graphene oxide-incorporated biomaterials", Seoul National University Graduate School: Department of Chemical and Biological Engineering, 2017, pp. 1-69.

(Continued)

*Primary Examiner* — Tracy Vivlemore
*Assistant Examiner* — Eric J Rogers
(74) *Attorney, Agent, or Firm* — Vorys, Sater, Seymour and Pease LLP; Mih Suhn Koh

(57) ABSTRACT

Provided is a composition capable of promoting osteogenic differentiation of stem cells, comprising, as active ingredients, a bone and cartilage progenitor cell culture solution and a multilayer graphene film, which promotes the differentiation of stem cells into specific cells, and thus is expected to be variously applicable in the in vivo/in vitro stem cell application fields.

8 Claims, 13 Drawing Sheets

Specification includes a Sequence Listing.

(56) References Cited

OTHER PUBLICATIONS

Ro et al., "Osteogenic priming of mesenchymal stem cells by chondrocyte-conditioned factors and mineralized matrix", Cell Tissue Res, 2015, vol. 362, No. 1, pp. 115-126.

* cited by examiner

ETCHING PROCESS     LAMINATION PROCESS     TRANSFER PROCESS

1. SYNTHESIZED SINGLE-LAYER GRAPHENE ON METAL FILM
2. ETCHING SOLUTION
3. SINGLE-LAYER GRAPHENE
4. SYNTHESIZED SINGE-LAYER/LAMINATED GRAPHENE ON METAL FILM
5. DISTILLED WATER
6. LAMINATED GRAPHENE
7. CELL CULTURE SUBSTRATE (a)

(b)

(c)

(d)

(e)

- Single: Osteogenic differentiation-inducing agent single treatment group
- Mix: Osteogenic differentiation-inducing agent + concentrated cell culture solution (200 μg/ml) mixed treatment group

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Beta-actin forward primer

<400> SEQUENCE: 1
atgaagccca gagcaaaaga                                               20

<210> SEQ ID NO 2
<211> LENGTH: 20
<212> TYPE: DNA
<213> ORGANISM: Artificial Sequence
<220> FEATURE:
<223> OTHER INFORMATION: Beta-actin reverse primer

<400> SEQUENCE: 2
ggggtgttga aggtctcaaa                                               20

<210> SEQ ID NO 3
<211> LENGTH: 20
<212> TYPE: DNA
<213> ORGANISM: Artificial Sequence
<220> FEATURE:
<223> OTHER INFORMATION: SOX9 forward primer

<400> SEQUENCE: 3
gctttctcgc atgaatctcc                                               20

<210> SEQ ID NO 4
<211> LENGTH: 20
<212> TYPE: DNA
<213> ORGANISM: Artificial Sequence
<220> FEATURE:
<223> OTHER INFORMATION: SOX9 reverse primer

<400> SEQUENCE: 4
ttggggaagg tgttctcttg                                               20

<210> SEQ ID NO 5
<211> LENGTH: 20
<212> TYPE: DNA
<213> ORGANISM: Artificial Sequence
<220> FEATURE:
<223> OTHER INFORMATION: COLLAGEN TYPE I forward primer

<400> SEQUENCE: 5
caaaccaggc gaaaggggtc                                              20

<210> SEQ ID NO 6
<211> LENGTH: 19
<212> TYPE: DNA
<213> ORGANISM: Artificial Sequence
<220> FEATURE:
<223> OTHER INFORMATION: COLLAGEN TYPE I reverse primer

<400> SEQUENCE: 6
aatggaccac ggcttccaa                                               19

<210> SEQ ID NO 7
<211> LENGTH: 20
<212> TYPE: DNA
<213> ORGANISM: Artificial Sequence
<220> FEATURE:
<223> OTHER INFORMATION: COLLAGEN TYPE II forward primer

<400> SEQUENCE: 7
aagatgttgt aggaccccga                                              20

<210> SEQ ID NO 8
<211> LENGTH: 20
<212> TYPE: DNA
<213> ORGANISM: Artificial Sequence
<220> FEATURE:
<223> OTHER INFORMATION: COLLAGEN TYPE II reverse primer

<400> SEQUENCE: 8
catctgcgcc gcaaagtttc                                              20

<210> SEQ ID NO 9
<211> LENGTH: 20
<212> TYPE: DNA
<213> ORGANISM: Artificial Sequence
<220> FEATURE:
<223> OTHER INFORMATION: RUNX2 forward primer

<400> SEQUENCE: 9
cagaccagca gcactccata                                              20

<210> SEQ ID NO 10
<211> LENGTH: 20
<212> TYPE: DNA
<213> ORGANISM: Artificial Sequence
<220> FEATURE:
<223> OTHER INFORMATION: RUNX2 reverse primer

<400> SEQUENCE: 10
ttgggcaagt ttgggtttag                                              20

<210> SEQ ID NO 11
<211> LENGTH: 20
<212> TYPE: DNA
<213> ORGANISM: Artificial Sequence
<220> FEATURE:
<223> OTHER INFORMATION: HUMAN GAPDH forward primer

<400> SEQUENCE: 11
gagtcaacgg atttggtcgt                                              20

<210> SEQ ID NO 12

```
<211> LENGTH: 20
<212> TYPE: DNA
<213> ORGANISM: Artificial Sequence
<220> FEATURE:
<223> OTHER INFORMATION: HUMAN GAPDH reverse primer

<400> SEQUENCE: 12
ttgattttgg agggatctcg                                                  20

<210> SEQ ID NO 13
<211> LENGTH: 19
<212> TYPE: DNA
<213> ORGANISM: Artificial Sequence
<220> FEATURE:
<223> OTHER INFORMATION: HUMAN RUNX2 forward primer

<400> SEQUENCE: 13
gacagcccca acttcctgt                                                   19

<210> SEQ ID NO 14
<211> LENGTH: 20
<212> TYPE: DNA
<213> ORGANISM: Artificial Sequence
<220> FEATURE:
<223> OTHER INFORMATION: HUMAN RUNX2 reverse primer

<400> SEQUENCE: 14
ccggagctca gcagaataat                                                  20

<210> SEQ ID NO 15
<211> LENGTH: 20
<212> TYPE: DNA
<213> ORGANISM: Artificial Sequence
<220> FEATURE:
<223> OTHER INFORMATION: HUMAN OSTEOCALCIN forward primer

<400> SEQUENCE: 15
agcaaaggtg cagcctttgt                                                  20

<210> SEQ ID NO 16
<211> LENGTH: 18
<212> TYPE: DNA
<213> ORGANISM: Artificial Sequence
<220> FEATURE:
<223> OTHER INFORMATION: HUMAN OSTEOCALCIN reverse primer

<400> SEQUENCE: 16
gcgcctgggt ctcttcat                                                    18
```

COMPOSITION FOR PROMOTING STEM CELL DIFFERENTIATION, COMPRISING PROGENITOR CELL CULTURE SOLUTION AND MULTILAYER GRAPHENE FILM, AND USE THEREOF

CROSS-REFERENCE TO RELATED APPLICATIONS

This application claims priority to and the benefit of Korean Patent Application No. 10-2018-0055015, filed on May 14, 2018 and International Patent Application No. PCT/KR2019/005765, filed on May 14, 2019, the disclosure of which is incorporated herein by reference in its entirety.

SEQUENCE LISTING

The Sequence Listing submitted in text format (.txt) filed on Nov. 13, 2020, named "SequenceListing.txt", created on Nov. 12, 2020 (2.90 KB), is incorporated herein by reference.

TECHNICAL FIELD

The present invention relates to a composition for promoting stem cell differentiation, comprising, as active ingredients, a progenitor cell culture solution and a multilayer graphene film, a use thereof, and the like.

BACKGROUND ART

Stem cells refer to a broad concept that collectively refers to undifferentiated cells having an ability to differentiate into cells of various types of body tissues, that is, sternness, and these stem cells are roughly divided into embryonic stem cells, which can be produced using embryos, adult stem cells, gametes, cancer stem cells, and the like. These stem cells not only can differentiate into various cells, but also can be variously used for suppression of excessive immune responses, mediators for gene therapy, production of various growth factors, and the like, and thus have been actively studied as a new therapeutic agent. However, the properties of stem cells should not be changed during culture and the differentiation potential thereof should be suppressed except for differentiation as necessary, but there has been a limitation in the growth regulation of these stem cells when an existing culture mechanism is used. Accordingly, there is an emerging need for a composition for stem cell differentiation, which not only enables stem cells to be cultured, but also enables stem cells to easily differentiate into target cells, in full consideration of the characteristics of stem cells.

Meanwhile, with the recent acceleration of aging worldwide, there is a trend that interest in various bone-related diseases such as osteoporosis, osteonecrosis, bone defect disease, and bone damage is increasing. Studies using particularly stem cells have been actively conducted for the treatment of these diseases, but the most studied field is the method of inducing the differentiation of mesenchymal stem cells into osteocytes. Examples of a compound that has been most commonly used as a differentiation-inducing agent include dexamethasone as a synthetic adrenocortical hormone, ascorbic acid, beta-glycerophosphate, and the like, but due to the insignificant effects thereof, studies have been conducted on a method of promoting osteogenic differentiation by further adding BMP-related proteins, TGF-β, or IGF-based recombinant proteins in order to induce effective osteogenic differentiation. However, methods for further adding a biological growth factor such as BMP-2 can promote bone cell differentiation, but has limitations such as immune response problems, short residual cycles, and cost issues (KR 10-2016-0043844 A1).

Therefore, the development of a composition for promoting differentiation, which is capable of promoting the in vivo or in vitro differentiation of stem cells into target cells and particularly promoting osteogenic differentiation of stem cells, is expected to be safely applicable in various stem cell application fields and capable of exhibiting high treatment effects during the damage of tissue or bone.

DISCLOSURE

Technical Problem

The present invention has been devised to solve the above-described problems in the related art, and an object thereof is to provide a composition for promoting stem cell differentiation, comprising, as active ingredients, a progenitor cell culture solution and a multilayer graphene film, a pharmaceutical composition for stem cell therapy using the same, a method of regulating the growth and differentiation of stem cells, and the like.

However, technical problems to be solved by the present invention are not limited to the aforementioned problems, and other problems that are not mentioned may be clearly understood by those with ordinary skill in the art from the following description.

Technical Solution

The present invention provides a composition for promoting stem cell differentiation, comprising a progenitor cell culture solution and a multilayer graphene film. The differentiation promotion preferably means the promotion of osteogenic differentiation of stem cells, and more preferably means the promotion of osteogenic differentiation of mesenchymal stem cells, but is limited thereto as long as it is a type that promotes differentiation in the composition of the present invention.

Further, the present invention provides a method of regulating the growth and differentiation of stem cells, the method comprising: culturing stem cells in the composition. The method is preferably a method of regulating the growth and differentiation of stem cells in vitro, but is not limited as long as it is a method using the composition for promoting stem cell differentiation of the present invention.

In addition, the present invention provides a pharmaceutical composition for preventing or treating a bone disease, comprising, as active ingredients, a progenitor cell culture solution, a multilayer graphene film, and stem cells.

Furthermore, the present invention provides a kit for preventing or treating a bone disease, comprising a progenitor cell culture solution, a multilayer graphene film, and stem cells.

Further, the present invention provides a pharmaceutical composition for cell therapy, comprising, as active ingredients, stem cells cultured in the composition. The pharmaceutical composition for cell therapy preferably means a pharmaceutical composition for treating a disease using stem cells, that is, a cell therapeutic agent, but is not limited thereto as long as it is a pharmaceutical composition comprising, as active ingredients, stem cells cultured in the composition of the present invention.

In an exemplary embodiment of the present invention, the progenitor cells may be bone and cartilage progenitor cells (osteochondroprogenitor cells), and the progenitor cells may be preferably osteochondroprogenitor cells of a starter chick, and are more preferably Sox9 protein-positive cells isolated from the ilium of the starter chick, but are not limited thereto.

In another exemplary embodiment of the present invention, the culture solution may be a culture solution from which cells are removed after progenitor cells are cultured, more preferably a culture solution from which cells are removed after progenitor cells are cultured in a serum-free medium, and even more preferably, a cell culture solution may be concentrated and used as a concentrated cell culture solution, but the culture solution is not limited thereto as long as it is a culture medium in which progenitor cells are cultured. The culture solution means a solution remaining after cells are cultured in a liquid medium for a certain period of time and then removed, and may include all of growth factors secreted from cells and proteins such as cytokines during the culture period and the nutritional ingredients and the like remaining after consumption during the cell culture, and may also be used as a dry powder by drying the same.

In still another exemplary embodiment of the present invention, the multilayer graphene film may preferably be a carbon laminate of 2 to 10 layers of graphene, more preferably 2 to 7 layers of graphene, even more preferably 2 to 5 layers of graphene, and even further more preferably 2 to 4 layers of graphene, but the number of layers is not limited thereto as long as it is a number capable of promoting differentiation of stem cells. Further, the multilayer graphene film may form wrinkles having a width of 20 to 60 nm, and additionally, may allow cell adhesion molecules to be attached to the surface thereof, and the cell adhesion molecules may be preferably lysine, fibronectin, fibrinogen, laminin, vitronectin, and the like, more preferably poly-D-lysine or poly-L-lysine, but are not limited as long as they are cell adhesion factors capable of increasing the attachment ability of cells. In addition, the surface may also be patterned using electron beam lithography, photolithography, and the like, and a method of patterning the graphene film is limited thereto as long as it is a method known to be used for stem cell culture.

In yet another exemplary embodiment of the present invention, the stem cells may be preferably embryonic stem cells, adult stem cells, and the like, more preferably mesenchymal stem cells, adipose-derived stem cells, hematopoietic stem cells, neural stem cells, and the like which are adult stem cells, but are not limited thereto as long as they are stem cells whose differentiation is promoted in the composition of the present invention.

In yet another exemplary embodiment of the present invention, the surface of the multilayer graphene film may be coated with the progenitor cell culture solution, and the coating may be performed by a drying method, an application method, a printing method, a dipping method, a binding method using a chemical, and the like, but the method is not limited thereto as long as it is a method of coating the surface of a solid with a generally known liquid.

In yet another exemplary embodiment of the present invention, the bone disease may preferably be a bone disease, a cartilage disease, and the like, more preferably osteoporosis, osteonecrosis, a bone injury, osteomalacia, rickets, osteitis fibrosa, an adynamic bone disease, a metabolic bone disease, nonunion of fracture, degenerative arthritis, a joint injury caused by trauma, arthrosis deformans, cartilaginous dystrophy, a degenerative disc disease, a meniscus injury, a cartilage injury, a cartilage defect, and the like, but is not limited thereto as long as it is a disease which can be treated using osteogenic differentiation of stem cells.

Furthermore, the present invention provides a method of treating a bone disease, the method comprising: administering, to an individual, stem cells cultured in the composition for promoting stem cell differentiation, or administering, to an individual, a composition comprising, as active ingredients, a progenitor cell culture solution, a multilayer graphene film, and stem cells.

Further, the present invention provides a use of a composition comprising, as active ingredients, stem cells cultured in the composition for promoting stem cell differentiation, or a composition comprising, as active ingredients, a progenitor cell culture solution, a multilayer graphene film, and stem cells, for treating a bone disease.

Advantageous Effects

The composition for promoting stem cell differentiation, comprising a progenitor cell culture solution and a multilayer graphene film according to the present invention has a differentiation efficiency which is 2-fold or higher compared to an existing method of inducing osteoblasts, and can promote differentiation of stem cells using only a carbon atom, which is harmless to the human body, and a culture solution from which cells of progenitor cells are removed, so that the composition is expected to be widely usable in the treatment of diseases using various stem cells because it is possible to remarkably reduce the occurrence of side effects. Further, the composition is expected to be applicable to various fields using stem cells because it is possible to variously change the type of substrate which is coated with graphene and to add various additives during a process of coating graphene with a progenitor cell culture solution. In addition, the composition is expected to enable the development of a culture vessel which promotes osteoblast differentiation for in vitro bone cell induction experiments, a bone chip for bone tissue regeneration, and the like. Therefore, the present invention is expected to be easily applicable to various research fields such as such as the medical/biotechnology industry, nanoscience, the microscope industry, the materials industry, agriculture and the fishing industry.

MODES OF THE INVENTION

Figure 1:
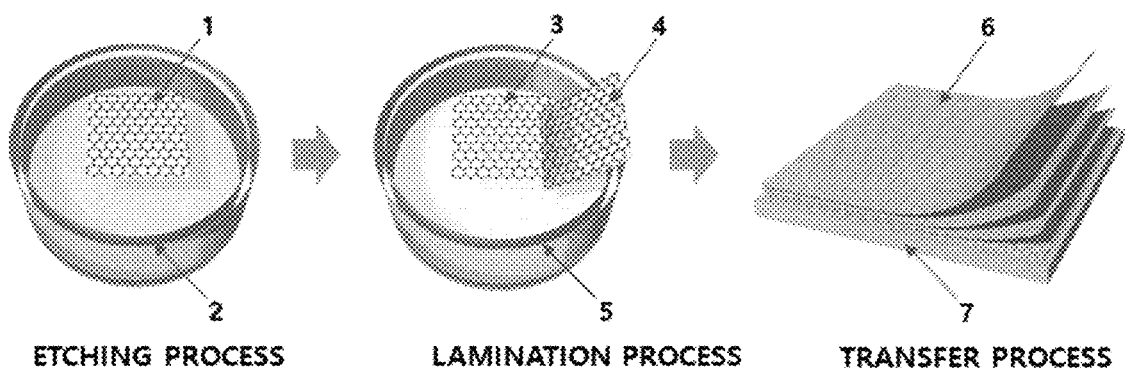
FIG. 1 is a view schematically illustrating a method of manufacturing a graphene film according to an exemplary embodiment of the present invention.

Since it was confirmed that the composition for promoting stem cell differentiation, comprising a progenitor cell culture solution and a multilayer graphene film according to the present invention may effectively promote the differentiation of stem cells and may promote osteo-specific differentiation of mesenchymal stem cells having multipotency compared to the existing stem cell differentiation methods, stem cells cultured in the composition comprising a progenitor cell culture solution and a multilayer graphene film according to the present invention may be used in various in vivo/in vitro stem cell application fields, such as osteogenesis and treatment of bone diseases.

As used herein, graphene is a material having an atom-sized honeycomb structure made of carbon atoms, and is a next-generation new material having a thickness of 0.2 nm and extremely high physical and chemical stability, and the multilayer graphene film of the present invention is a general term for a structure in which single-layered graphene is laminated.

As used herein, progenitor cells are also called committed stem cells, and the like, and when cells corresponding to progeny (for example, X) are revealed to express specific differentiation formation, undifferentiated parent cells that do not express a differentiation trait are referred to as progenitor cells of X. The osteochondroprogenitor cells of the present invention are cells which have the ability to differentiate into bone and cartilage, but whose fate has not yet been determined, are cells in a stage between mesenchymal stem cells and osteoprogenitor cells which differentiate into osteogenic cells or in a stage between mesenchymal stem cells and chondroprogenitor cells which differentiate into chondrocytes, and are present in the bone marrow as well as in bone tissue. Such a culture solution (broth) of progenitor cells may be preferably a culture medium from which the progenitor cells are removed after the progenitor cells are cultured in the medium, and more preferably a culture medium of the progenitor cells cultured in a serum-free medium, and such a culture solution may be prepared as a concentrated culture solution, and the concentrated culture solution may be prepared by filtering cells and cell debris from the culture solution, in which progenitor cells are cultured, using a vacuum filtration device or the like and concentrating the filtered culture solution 2 to 1,000-fold, preferably 50 to 150-fold using a filter, but the culture solution is not limited thereto.

As used herein, the "stem cell" refers to a general concept of undifferentiated cells having the ability to differentiate into various types of tissue cells, that is, undifferentiated cells having stemness. These stem cells are roughly divided into embryonic stem cells which may be produced using embryos, adult stem cells, germ cells (gametes), cancer stem cells, and the like, the embryonic stem cells refer to a stage of a cell mass before forming a specific organ within 14 days after fertilization, and recently, embryonic stem cells are also produced from normal cells through dedifferentiation. Therefore, the stem cells are not limited thereto as long as the stem cells are cells capable of differentiating into all cells and tissues constituting the body. Adult stem cells are extracted from umbilical cord blood, bone marrow, blood and the like, and refer to primitive cells just before differentiation into cells of specific organs such as bone, the liver and blood. Germ cells are cells that transmit genetic information to the next generation through reproduction, and although human beings have sperm and ova, germ cells are not limited thereto. Cancer stem cells refer to cancer cells in a comprehensive sense, which have self-renewal or differentiation capabilities which are a unique ability of stem cells. Cancer stem cells generally may have resistance to anticancer agents by proliferating at a slow rate different from that of general cancer cells under normal tumor growth conditions (referring to a state where there is no cellular stress because the nutrients (glucose) necessary for cell growth are sufficient and the growth condition of the tumor microenviroment is abundant) or maintaining a dormant state, and for example, the expression of transcriptional regulatory factors such as PGC-1α may be controlled unlike normal tumor cells, so that the functions of major metabolic regulators may differ from those of general cancer cells. Cancer stem cells comprehensively refer to cells with the ability to invade and metastasize, which have acquired resistance to cell apoptosis in a nutrient-deficient state through the regulation of a cell signal transduction system, which is mechanically linked with the different metabolic regulation abilities. However, cancer stem cells are not limited thereto as long as cancer stem cells are cell capable of differentiating into general cancer cells.

As used herein, a pharmaceutical composition for stem cell therapy refers to a drug used for the purpose of treatment, diagnosis, and prevention, using a cell or tissue prepared through isolation from an individual, culture and specific manipulation (US FDA regulation), and specifically, it refers to a drug used for the purpose of treatment, diagnosis, and prevention through a series of actions of in vitro multiplying and screening living autologous, allogenic and xenogenic cells or changing the biological characteristics of cells by other methods in order to recover the functions of cells or tissues.

As used herein, differentiation refers to a procedure in which while stem cells divide, proliferate, and grow, their structures and functions are specialized with each other, and the stem cells are transformed into cells of different tissues.

As used herein, prevention refers to a general concept of blocking the occurrence of a bone disease and the like by administration of the composition according to the present invention, preferably includes both primary prevention to prevent the occurrence of the disease and the like in advance before the occurrence, and secondary prevention to early detect and timely treat the disease and the like, but is not limited thereto as long as it is a process and/or activity which addresses the bone disease before the occurrence of the bone disease.

As used herein, the "treatment" refers to all actions in which symptoms such as a bone disease are ameliorated or advantageously changed by administering the composition according to the present invention.

As used herein, the "individual" refers to a subject to which the composition of the present invention may be administered, and the subject is not limited.

As used herein, the "pharmaceutical composition" may take the form of a capsule, a tablet, a granule, an injection, an ointment, a powder, or a beverage, and the pharmaceutical composition may target humans. The pharmaceutical composition is not limited thereto, but may be used by being formulated into the form of an oral dosage form such as powder, granules, a capsule, a tablet, and an aqueous suspension, an external preparation, a suppository, and a sterile injectable solution. The pharmaceutical composition of the present invention may include a pharmaceutically acceptable carrier. As the pharmaceutically acceptable carrier, a binder, a lubricant, a disintegrant, an excipient, a solubilizing agent, a dispersing agent, a stabilizer, a suspending agent, a colorant, a flavoring agent, and the like may be used when orally administered, in the case of injection, a buffering agent, a preservative, an analgesic, a solubilizer, an isotonic agent, a stabilizer, and the like may be mixed and used, and in the case of topical administration, a base, an excipient, lubricant, a preservative, and the like may be used. The formulation of the pharmaceutical composition of the present invention may be variously prepared by mixing the pharmaceutical composition of the present invention with the pharmaceutically acceptable carrier as described above. For example, the formulation may be prepared in the form of a tablet, a troche, a capsule, an elixir, a suspension, a syrup, a wafer, and the like when orally administered, and in the case of an injection, the injection may be formulated into unit dosage ampoules or in multiple dosage forms. The pharmaceutical composition of the present invention may be formulated into other solutions, suspensions, tablets, capsules, sustained-release preparations, and the like.

Meanwhile, as examples of suitable carriers, excipients and diluents for formulation, it is possible to use lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, or the like. Further, the pharmaceutical composition of the present invention may further include a filler, an anticoagulant, a lubricant, a wetting agent, a flavoring agent, an emulsifying agent, an antiseptic, and the like.

The route of administration of the pharmaceutical composition according to the present invention includes, but is not limited to, oral, intravenous, intramuscular, intraarterial, intramedullary, intrathecal, intracardiac, transdermal, subcutaneous, intraperitoneal, intranasal, enteral, topical, sublingual or rectal. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The pharmaceutical composition of the present invention may also be administered in the form of a suppository for rectal administration.

The pharmaceutical composition of the present invention varies depending on various factors including the activity of the specific compound used, age, body weight, general health, sex, diet, time of administration, route of administration, rate of excretion, drug combination and the severity of the particular disease to be prevented or treated, and the dosage of the pharmaceutical composition varies depending on the condition of the patient, the body weight, the degree of disease, the form of drug, the route of administration and duration, but may be appropriately selected by a person skilled in the art, and may be 0.0001 to 500 mg/kg or 0.001 to 500 mg/kg daily. The administration may be carried out once daily, and may be divided into several times. The dosage is not intended to limit the scope of the present invention in any way. The pharmaceutical composition according to the present invention may be formulated into pills, dragees, capsules, solutions, gels, syrups, slurries, and suspensions.

As used herein, the "kit" refers to a therapeutic device including the progenitor cell culture solution, multilayer graphene and stem cells of the present invention, each of which may be included in different compartments and/or bottles and may be all included in one, and as the stem cells, personalized stem cells may also be used and it is possible to preferably include a composition including therapeutic undifferentiated stem cells, a progenitor cell culture solution and a multilayer graphene as active ingredients, but the present invention is not limited thereto.

Hereinafter, the following Examples for helping the understanding of the present invention will be suggested. However, the following Examples are provided only to more easily understand the present invention, and the contents of the present invention are not limited by the following Examples.

EXAMPLES

Example 1: Manufacture of Graphene Film

A graphene film was manufactured using chemical vapor deposition (CVD). In order to manufacture the graphene film, a nickel film or copper film which is a catalyst was loaded into a quartz tube. Then, carbon was allowed to enter between or on the surface of the catalyst bed by introducing methane or acetylene gas into the tube at 1000° C., and after reaction for 30 minutes to 60 minutes, a single-layer graphene (SLG) film was manufactured by cooling the tube to room temperature as in the natural cooling rate and using an etching solution such as an ammonium persulfate (APS) or iron (III) chloride solution to remove the catalyst film. In order to deliver the manufactured graphene to a substrate, poly(methyl methacrylate)(PMMA) was spin-coated on the graphene, and the PMMA/graphene was transferred to a glass substrate, a silicon wafer and a cell culture plate. Then, after PMMA was removed using acetone, acetone was removed using distilled water. Further, a multi-layer graphene (MLG) film was manufactured by laminating ten layers of the produced single-layer graphene one layer at a time. The transfer method was performed in the same manner as with the single-layer graphene film. The method of manufacturing a graphene film is schematically illustrated in FIG. 1. Then, the manufactured graphene film was confirmed using a scanning electron microscope (SEM). The results are illustrated in FIG. 2.

Figure 2:
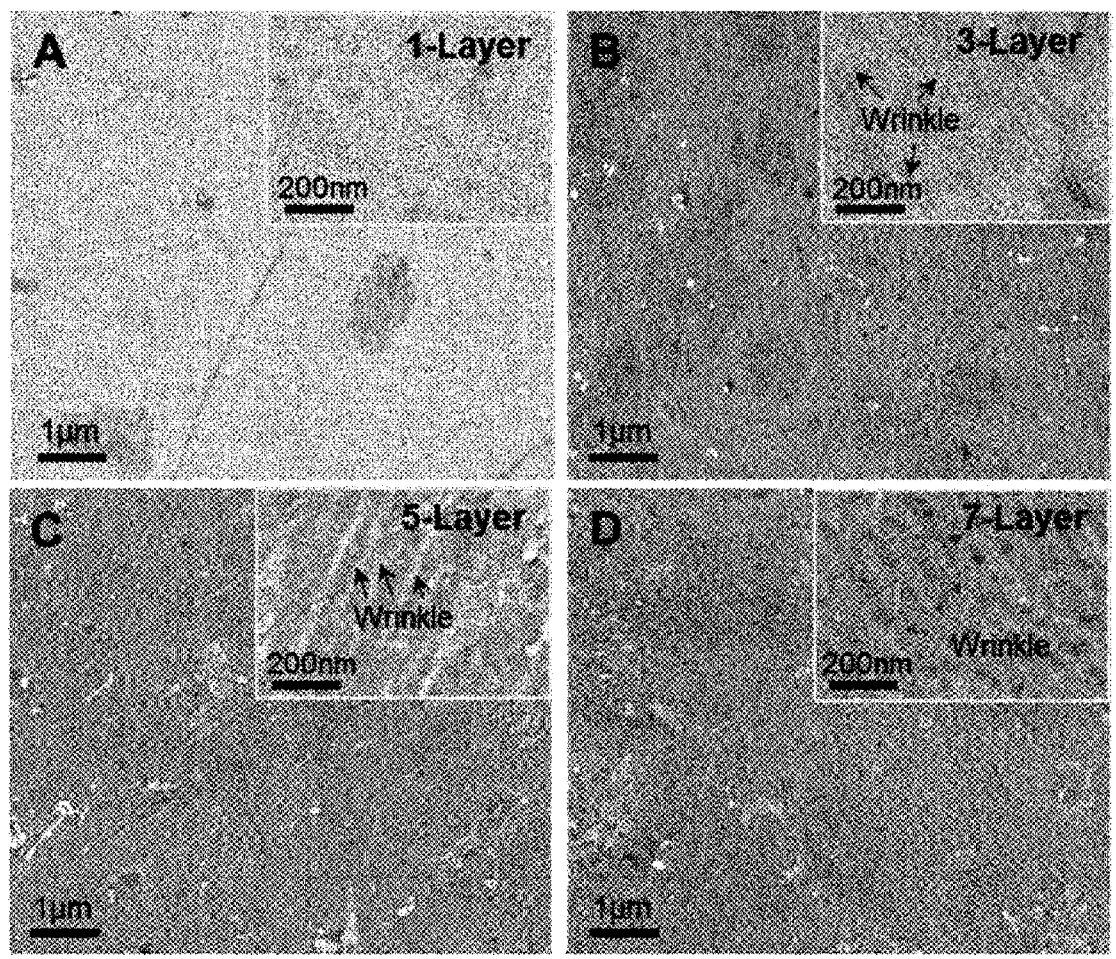
FIG. 2 is a view illustrating the results of observing a graphene film manufactured according to an exemplary embodiment of the present invention with a scanning electron microscope.

As illustrated in FIG. 2, it was confirmed that a single-layer or multi-layer graphene film was manufactured according to the planned number of layers, and that as the number of graphene layers was increased, wrinkles with a width of about 30 to 50 nm were formed and increased on the graphene surface.

Example 2: Isolation of Osteochondroprogenitor Cells in Bone Marrow and Preparation of Culture Solution of Said Cells 2.1. Isolation of Osteochondroprogenitor Cells After femur and tibia portions were collected from both legs of a chick within 4 days after hatching, the parts were washed twice, and then the muscles and tendons attached to the bones were cleanly removed, and then the remaining parts were washed twice. A phosphate-buffered saline (PBS) solution supplemented with 1% antibiotic and an antibacterial agent was used in all washing processes. Then, the hardened parts on both sides of the bone were removed using surgical scissors, a hole was created with an 18 gauge (G) injection needle, PBS supplemented with 1% antibiotic and 2% fetal bovine serum (FBS) was placed in a 3-ml medical syringe to which an injection needle was attached and pushed into the hole at the tip of the bone to collect a matrix in the bone. The matrix was collected three times in both directions, with the femur being collected using an 18G needle and the tibia being collected using a 20G needle.

Figure 3:
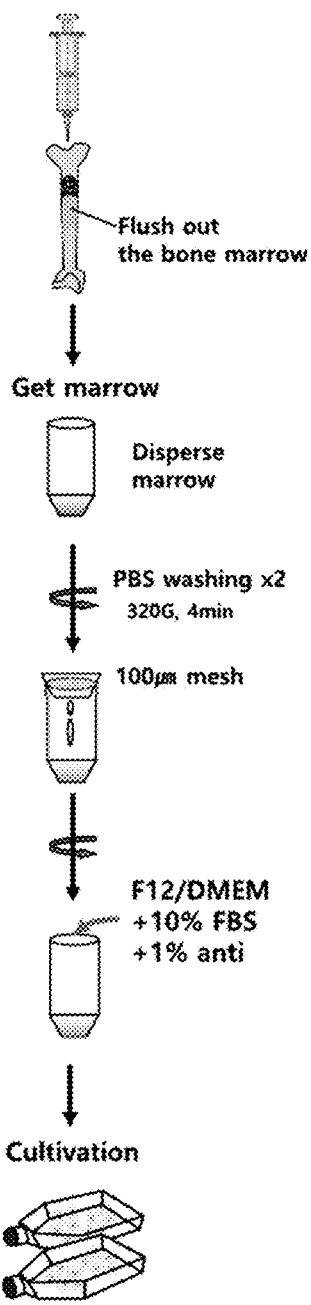
FIG. 3 is a view schematically illustrating a method of obtaining and culturing bone and cartilage progenitor cells of a chick according to an exemplary embodiment of the present invention, and a method of preparing a culture solution of the cells.
Figure 3:
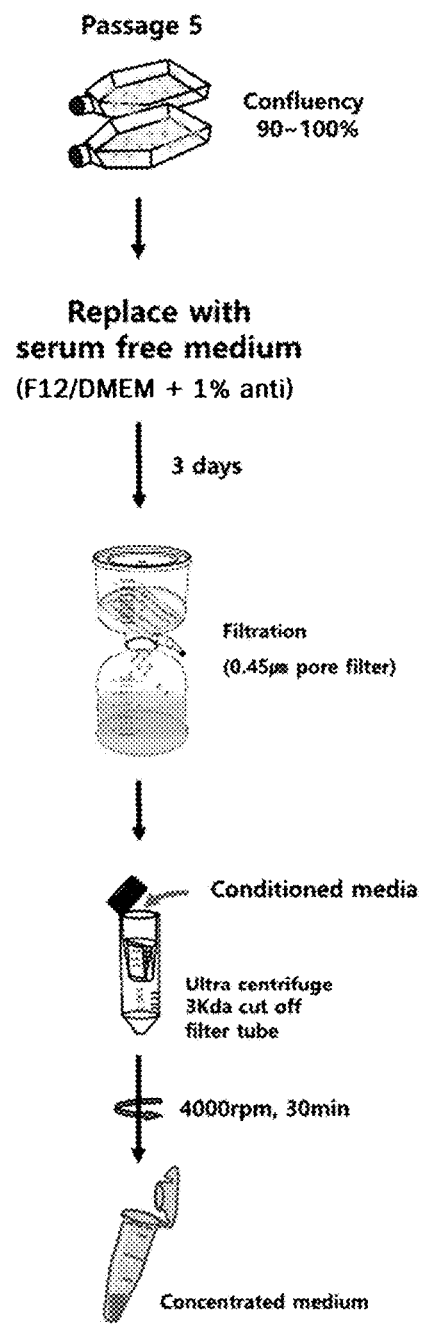

Matrices collected from a total of 4 bones per animal were collected in a 14 ml round bottom tube and allowed to pass through the syringe used for collection 10 times to homogenize the tissue, and then a 100 μm pore mesh was placed on a 50 ml conical tube, and the homogenized matrices were filtered to filter bone fragments or debris, and the like introduced at the time of collection. Then, the tube was filled with PBS and centrifuged at 320 g for 4 minutes to remove the supernatant, and a cell pellet, which is a mass of cells precipitated in the lower part of the tube, was obtained. Then, 5 mL of an F12/DMEM medium was added to the obtained cell pellet, and unicellular osteochondroprogenitor cells were obtained by pipetting. The method of obtaining and culturing chick osteochondroprogenitor cells and the method of obtaining a culture medium of the said cells are schematically illustrated in FIG. 3.

2.2. Culture of Osteochondroprogenitor Cells

Chick progenitor cells obtained in the same manner as in Example 2.1 were inoculated into an F12/DMEM medium supplemented with 3.151 g/L D-glucose, 365 mg/L (2.5 mM) L-glutamine, 55 mg/L (0.5 mM) sodium pyruvate, 10% FBS, and a 1% antibiotic-antibacterial agent, and cultured under conditions of a humidity of about 90% and a temperature of 37° C. in a 5% $CO_2$ incubator. For subculture, when the confluency of cells reached about 80 to 90%, the cells were washed twice with PBS and then treated with 0.25% Trypsin-EDTA for 2 minutes, a cell suspension was collected and centrifuged at 320 g for 4 minutes to collect cells, and then, the number of cells and cell viability were checked using some cells, and then the cells were again subcultured 3 times.

2.3. Characteristic Analysis of Osteochondroprogenitor Cells

Histological staining was performed by hematoxylin-eosin staining (H&E staining) to analyze the morphological state in the ilium of a starter chick. After the ilium of a 4-day-old chick were immersed in a 4% paraformaldehyde fixative and fixed at room temperature for 24 hours, the fixed tissue was washed and subjected to decalcification and dehydration processes, and then was prepared as a paraffin block using paraffin. Then, a section was prepared by cutting the prepared paraffin block to a thickness of 6 mm, and then placed on a heating block at 60° C. for 45 minutes to perform deparaffinization. Then, the section was washed three times for 5 minutes each by being immersed in a xylene solution, and immersed three times in 100% ethanol for 3 minutes each, twice in 95% ethanol for 2 minutes each, twice in 70% ethanol for 2 minutes each, and twice in distilled water for 2 minutes each for hydration. The paraffin section which had been subjected to hydration process was immersed in a 1% hematoxylin solution for 30 seconds for staining, then washed once with distilled water, further reacted in 0.25% hydrogen chloride (HCl) for 1 second, and then washed with distilled water. Then, the section was allowed to react with 10% lithium carbonate as a mordant for 2 to 4 seconds, and then washed with distilled water. Then, the cytoplasm was stained by treating the section with eosin for 2 seconds, subjected to final dehydrogenation and clarification steps using 95% ethanol and 100% ethanol, and then mounted and observed under a microscope, and photographs were obtained. The results are illustrated in FIG. 4A.

Figure 4:
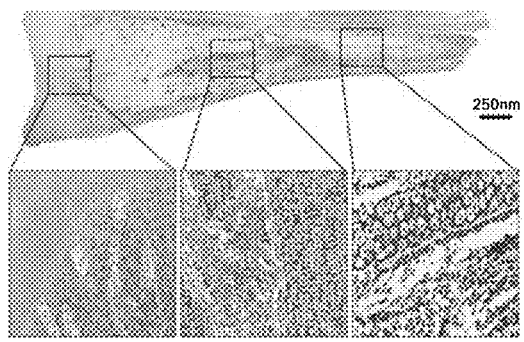
FIG. 4 is a view illustrating the results of morphologically and genetically analyzing progenitor cells isolated from the ilium of a chick according to an embodiment of the present invention, (a) is a view illustrating the results of confirming the inside of the ilium of a 4-day-old chick by H&E staining, (b) is a view illustrating the results of observing cells recovered from the ilium of the chick and cultured under an optical microscope, (c) is a view illustrating the results of confirming protein expression levels of the cells, (d) is a view illustrating the results of confirming gene expression levels of the cells, and (e) is a view illustrating the results of confirming the multipotency of the cells.
Figure 4:
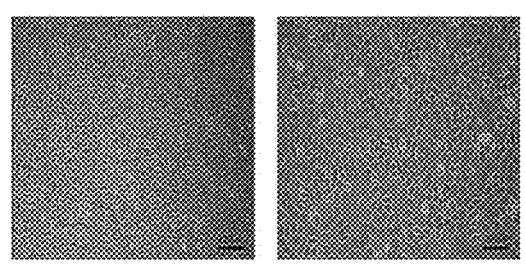
Figure 4:
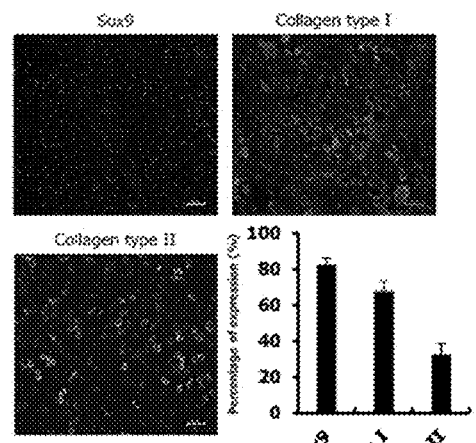
Figure 4:
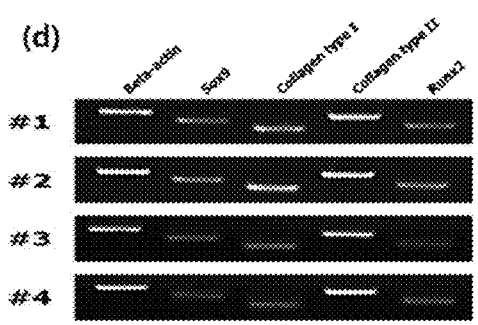
Figure 4:
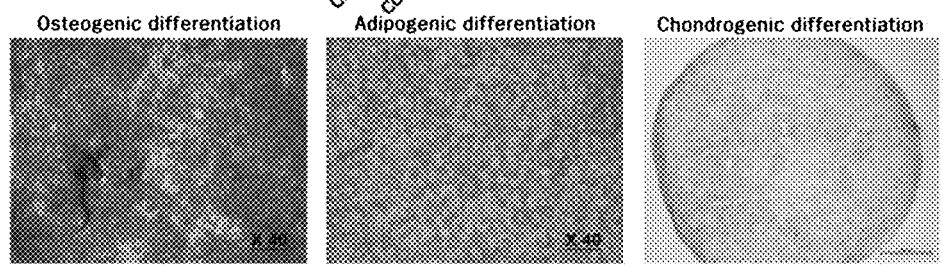

As illustrated in FIG. 4A, it was confirmed that 60% or more of the total area of the ilium of a 4-day-old chick was filled with chondrocytes in various stages, and the epiphysis still maintained a hyaline cartilage state in which a secondary ossification center had not been produced.

Further, the morphologies of cells collected and cultured in the same manner as in Examples 2.1 and 2.2 were photographed under an optical microscope and confirmed. The results are illustrated in FIG. 4B.

As illustrated in FIG. 4B, it was confirmed that the osteochondroprogenitor cells of the starter chick had a small and cuboidal shape, which could be confirmed to be different from that of general mesenchymal stem cells having a spindle shape.

Then, in order to confirm the gene expression of the progenitor cells that were collected in the same manner as in Examples 2.1 and 2.2 and subcultured 5 times, an analysis of the expression levels of Sox9, Collagen type I, Collagen type II, and Runx2 genes and expression levels of Sox9, Collagen type I, and Collagen type II proteins was performed. Specifically, in order to analyze the protein expression levels, the said cells were fixed with 4% paraformaldehyde at room temperature for 15 minutes, and then the fixed cells were washed three times using PBS, and blocking was performed with a 10% normal goat serum solution diluted in PBS for 1 hour. Then, after each protein was treated with a primary antibody and bounded by being allowed to react at 4° C. for 18 hours, the unbound primary antibodies were removed by washing twice with PBS, and the protein was treated with a secondary antibody with fluorescence attached to the primary antibody (manufactured by Santa Cruz Biotechnology) and allowed to react at room temperature for 2 hours. After the reaction was completed, the protein was washed twice with PBS to remove unbound antibodies and treated with a 4',6-diamidine-2'-phenylindole (DAPI) solution for 1 minute to stain the nuclei. After the stained cells were mounted with a mounting solution, the presence or absence of expression was analyzed using a fluorescence microscope. The results are illustrated in FIG. 4C. Furthermore, for gene expression analysis, RNA was extracted from cells by a phenol-chloroform extraction method using a TRIzol reagent, and after cDNA was synthesized using a reverse transcription-polymerase chain reaction (RT-PCR), a polymerase chain reaction (PCR) was performed using primers specific for each gene by employing Sox9, Collagen type I, Collagen type II, Runx2, and a β-actin gene, which is a housekeeping gene, as a control gene. Information on primers used for PCR is shown in the following Table 1, and the PCR products were confirmed by electrophoresis on a 1% agarose gel. The results are illustrated in FIG. 4D.

TABLE 1

| Gene | SEQ ID NO | Base sequence |
|---|---|---|
| β-actin | 1 | 5'-ATGAAGCCCAGAGCAAAAGA-3' |
|  | 2 | 5'-GGGGTGTTGAAGGTCTCAAA-3' |
| Sox9 | 3 | 5'-GCTTTCTCGCATGAATCTCC-3' |
|  | 4 | 5'-TTGGGGAAGGTGTTCTCTTG-3' |
| Collagen type I | 5 | 5'-CAAACCAGGCGAAAGGGGTC-3' |
|  | 6 | 5'-AATGGACCACGGCTTCCAA-3' |
| Collagen type II | 7 | 5'-AAGATGTTGTAGGACCCCGA-3' |
|  | 8 | 5'-CATCTGCGCCGCAAAGTTTC-3' |
| Runx2 | 9 | 5'-CAGACCAGCAGCACTCCATA-3' |
|  | 10 | 5'-TTGGGCAAGTTTGGGTTTAG-3' |

As illustrated in FIGS. 4C and 4D, it was confirmed that all the characteristic genes of osteochondroprogenitor cells, bone progenitor cells, or cartilage progenitor cells were expressed, and Sox9, Collagen type I, and Collagen type II proteins were also expressed. Through the results, it could be confirmed that osteochondroprogenitor cells were normally obtained from the starter chick.

2.4. Confirmation of Differentiation Potential of Isolated Osteochondroprogenitor Cells In order to confirm whether the osteochondroprogenitor cells collected and cultured in the same method as in Examples 2.1 and 2.2 have multipotency, differentiation into bone cells, adipocytes, and chondrocytes was induced, respectively. For differentiation into bone cells, differentiation was induced for 21 days while replacing a high glucose DMEM culture solution supplemented with $10^{-7}$ M dexamethasone, 0.05 mM ascorbate-2-phosphate, 10 mM β-glycerophosphate, 10% FBS, and 1% antibiotic once every 3 days. After induction of differentiation, differentiation into bone cells was confirmed by performing Alizarin Red S (ARS, Sigma) staining. For differentiation into adipocytes, differentiation was induced for 21 days while replacing a high-glucose DMEM culture solution supplemented with $10^{-6}$ M dexamethasone, 0.5 mM 3-isobutyl1-methylxanthine (IBMX), 0.1 mM indomethacin, 10 μg/ml bovine insulin (pH 2.5), 10% FBS, and 1% antibiotic once every 3 days. After induction of differentiation, differentiation into adipocytes was confirmed by performing Oil Red O(ORO, Sigma) staining. For differentiation into cartilage cells, differentiation was induced for 21 days while replacing a high glucose DMEM culture solution supplemented with 10 ng/ml TGF-β1, $10^{-7}$ M dexamethasone, 1% ITS, 1.25 mg/ml BSA, 5 μg/ml linoleic acid, 50 μg/ml ascorbic acid-2-phosphate, 40 μg/ml L-proline, 10% FBS, and 1% antibiotic once every 3 days. After induction of differentiation, differentiation into cartilage cells was confirmed by performing Alcian blue staining. The results are illustrated in FIG. 4E.

As illustrated in FIG. 4E, it was confirmed that the osteochondroprogenitor cells obtained by the method of the present invention differentiated into bone cells and cartilage cells, but did not differentiate into adipocytes. Through the results, it could be confirmed that the osteochondroprogenitor cells obtained by the method of the present invention were osteochondroprogenitor cells having the differentiation potential to differentiate into bones and cartilage.

2.5. Preparation of Serum-Free Culture Solution of Osteochondroprogenitor Cells

In order to prepare a serum-free culture solution of osteochondroprogenitor cells, the culture solution was removed and washed three times with cold PBS when the confluency of the cells collected in the same manner as in Examples 2.1 and 2.2 and subcultured 5 times reached about 90 to 100%. Then, after a serum-free F12/DMEM supplemented with 3.151 g/L D-glucose, 657 mg/L (4.5 mM) L-glutamine, 110 mg/L (1 mM) sodium pyruvate, and a 1% antibiotic-antibacterial agent was added thereto, cells were cultured under conditions of a humidity of about 90% and a temperature of 37° C. in a 5% $CO_2$ incubator for 3 days, and a serum-free culture solution of osteochondroprogenitor cells was prepared by collecting the supernatant. Then, in order to prepare a concentrated solution of the collected serum-free culture solution, the remaining cells and cell debris were cleanly removed by filtering the serum-free culture solution with a disposable vacuum filtration device (0.45 μm pore size, Corning). Then, a serum-free culture concentrated solution was prepared by concentrating the filtered culture solution 100-fold using an ultra-centrifugal filter (3K Decutoff, Amicon). The protein concentration of the concentrated culture solution was 2 to 3 mg/ml, and the prepared concentrated culture solution was aliquoted at a volume of 500 µg (protein amount) and stored at −20° C. Then, the concentrated culture solution was slowly thawed at 4° C. in a refrigerator and used when used in an experiment.

Example 3: Acquisition of Human Adipose Tissue-Derived Mesenchymal Stem Cells and Analysis of Characteristics Thereof 3.1. Isolation and Culture of Single Mesenchymal Stem Cell in Adipose Tissue A collected visceral adipose tissue (omental adipose tissue) was washed three times using cold PBS supplemented with a 1% antibiotic-antibacterial agent, and blood vessels, coagulated blood and connective tissues, which were attached to the washed tissue, were removed with forceps and surgical scissors, and the tissue was washed twice again. Then, after the washed tissue was placed in a 100 ml glass bottle and cut into 5 mm² or less using surgical scissors, a DMEM medium supplemented with 0.1% collagenase type I (Sigma-Aldrich) was added at twice the tissue volume, and the mixture was slowly stirred and reacted, such that an enzymatic reaction sufficiently occurred at 37° C. in a thermostat. After the enzymatic reaction was completed, the medium was collected, placed in a new tube, placed on ice and stored, and the enzymatic reaction was repeated once more while stirring the medium to which the new enzyme was added again with the tissue. After all the media collected primarily and secondarily were combined and filtered using a 100 µm pore mesh, the media were centrifuged at 320 g for 4 minutes to remove a pure adipose layer and collect a monocytic layer, the monocytic layer was washed twice using PBS, then an erythrocyte hemolytic solution (Gibco BRL) was added to remove erythrocytes, and the resulting mixture was allowed to react at room temperature for 10 minutes. After the reaction was completed, the cells were washed twice with PBS, and the cell number and cell viability were measured. Then, the cells were dispensed into an F12/DMEM medium supplemented with 5 ng/ml human recombinant basic fibroblast growth factor (hrbFGF, Gibco BRL), 10% FBS, and 1% antibiotic at a density of 1×10⁵ cells per cm² area of the plate, and cultured under conditions of a humidity of about 90% and a temperature of 37° C. in a 5% CO₂ incubator. After the cells were dispensed, the medium was replaced with a new medium every 3 days, and subculture was performed when the confluency reached 80 to 90%. After 5 passages, the cell morphology was photographed using a microscope, the characteristics were analyzed, and then the cells were used in the experiment. The results of microscopic observation are illustrated in FIG. 5A.

Figure 5:
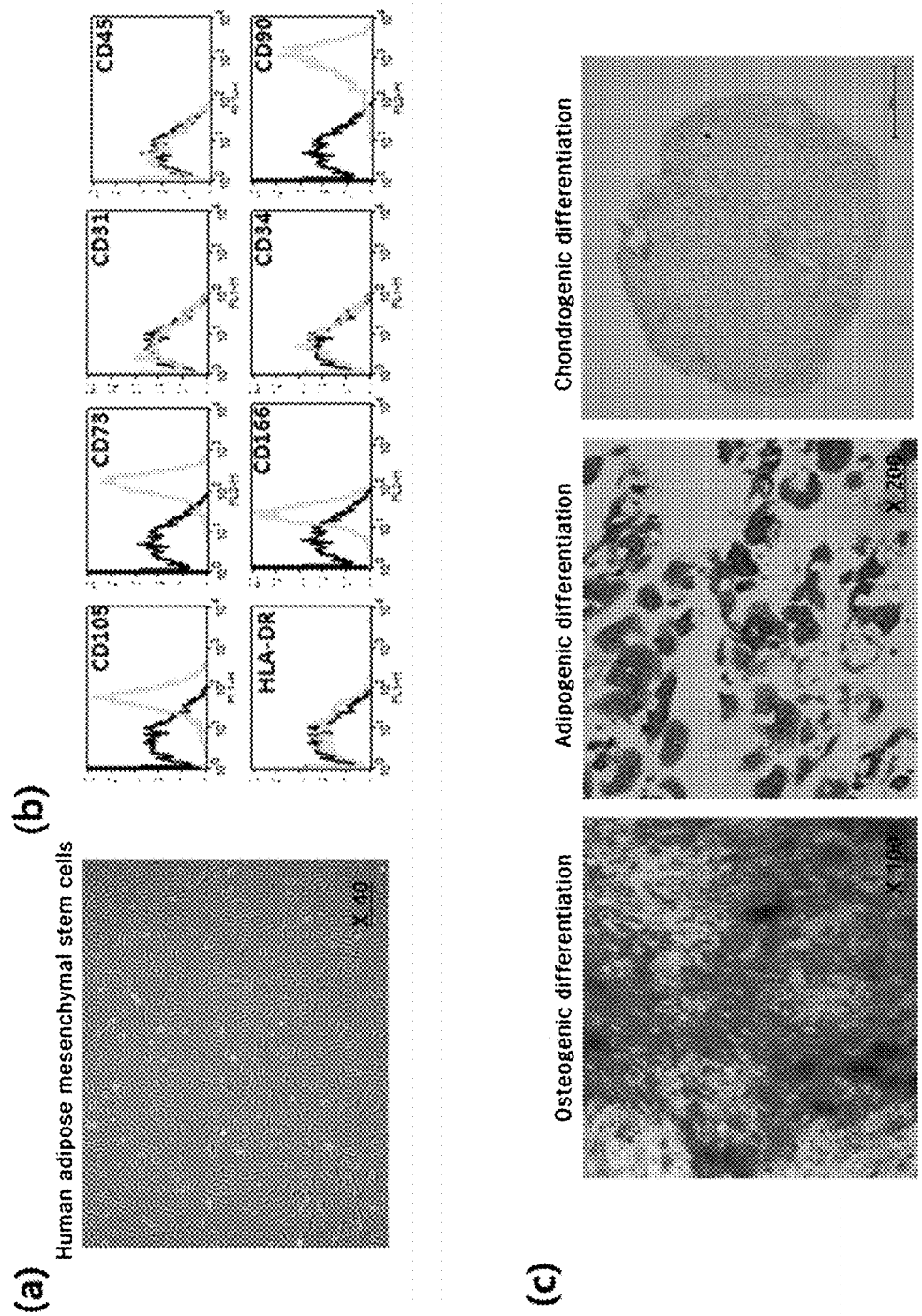
FIG. 5 is a view illustrating the results of analyzing human adipose-derived mesenchymal stem cells obtained according to an exemplary embodiment of the present invention, (a) is a view illustrating the results of observing mesenchymal stem cells under an optical microscope, (b) is a view illustrating the results of confirming markers of mesenchymal stem cells using FACS, and (c) is a view illustrating the results of confirming the multipotency of mesenchymal stem cells.

As illustrated in FIG. 5A, it was confirmed that spindle-shaped mesenchymal stem cells were normally obtained from human adipose tissue.

3.2. Confirmation of Cell Phenotype

In order to confirm the characteristics of the mesenchymal stem cells isolated and cultured in the same manner as in Example 3.1, the presence or absence of expression of CD105, CD73, CD31, CD45, HLA-DR, CD166, CD34, and CD90 was confirmed using a FACSCalibur (B&D Bioscience, CellQuest™ Pro). The results are illustrated in FIG. 5B.

As illustrated in FIG. 5B, CD31 (vascular endothelial cell marker), CD34 (hematopoietic stem cell marker), CD45 (hemocyte marker), and MHC class II (leukocyte antigen class II marker) antigens were negative, and middle lobe stem cells, and the mesenchymal stem cell markers CD105, CD73, CD166, and CD90 antigens were analyzed as positive. Through the results, it could be confirmed that the cells isolated by the method of the present invention normally had the characteristics of mesenchymal stem cells.

3.3. Confirmation of Multipotency

In order to confirm the multipotency of the mesenchymal stem cells isolated and cultured in the same manner as in Example 3.1, differentiation into bone cells, adipocytes and chondrocytes was induced, respectively. The induction and confirmation of differentiation were performed in the same manner as in Example 2.4. The results are illustrated in FIG. 5C.

As illustrated in FIG. 5C, it was confirmed that the mesenchymal stem cells isolated by the method of the present invention have multipotency capable of differentiating into bone cells, adipocytes, and chondrocytes.

Example 4: Osteogenic Differentiation Promoting Test of Human Adipose Tissue-Derived Mesenchymal Stem Cells 4.1. Induction of Differentiation into Bone Cells In order to confirm the effects of the concentrated culture solution of the present invention on the differentiation of stem cells, after human adipose tissue-derived mesenchymal stem cells isolated and cultured in the same manner as in Example 3.1 were cultured using an F12/DMEM medium supplemented with 10% FBS, 5 ng/ml hrbFGF, and 1% antibiotic, when the confluency reached 90%, differentiation into bone cells was induced by replacing a bone cell differentiation inducing medium supplemented with a 200 µg/ml culture concentrated solution with a low glucose DMEM medium supplemented with $10^{-7}$ M dexamethasone, 0.05 mM ascorbate-2-phosphate, 10 mM β-glycerophosphate, 10% FBS, and 1% antibiotic to culture cells for 14 days or 21 days. The medium was exchanged with a new medium once every 3 days. As controls, 1) a low glucose DMEM medium supplemented with 10% FBS and 1% antibiotic without any differentiation inducer, 2) a bone cell differentiation inducing medium (medium without addition of the concentrated culture solution), and 3) a low glucose DMEM medium (supplemented with a concentrated single culture solution) supplemented with 10% FBS and 1% antibiotic without any differentiation inducer supplemented with 200 µg/ml concentrated culture solution were used.

4.2. Confirmation of Alizarin Red S Staining

In order to confirm the efficiency of differentiation into bone cells after inducing differentiation into bone cells in the same manner as in Example 4.1, Alizarin Red S (ARS, Sigma) staining was performed. Since ARS has a property of binding to metal ions, it is possible to determine whether differentiation into bone cells occurred by staining calcium precipitation (mineralization) secreted from cells. Cells were fixed at room temperature for 15 minutes by treating a cell sample at the completion of differentiation with 4% paraformaldehyde (PFA). The fixed cells were washed twice with distilled water and treated with a 2% ARS staining solution at room temperature for 15 minutes. In this case, the ARS solution was used after adding ARS to distilled water having a pH of 4.5 to a concentration of 2%, using a magnetic bar to stir the ARS solution for 18 hours, and filtering the ARS solution. After the stained cells were washed five times with distilled water, the presence or absence of ARS staining was confirmed under an optical microscope and photographed. The results are illustrated in FIG. 6.

Figure 6:
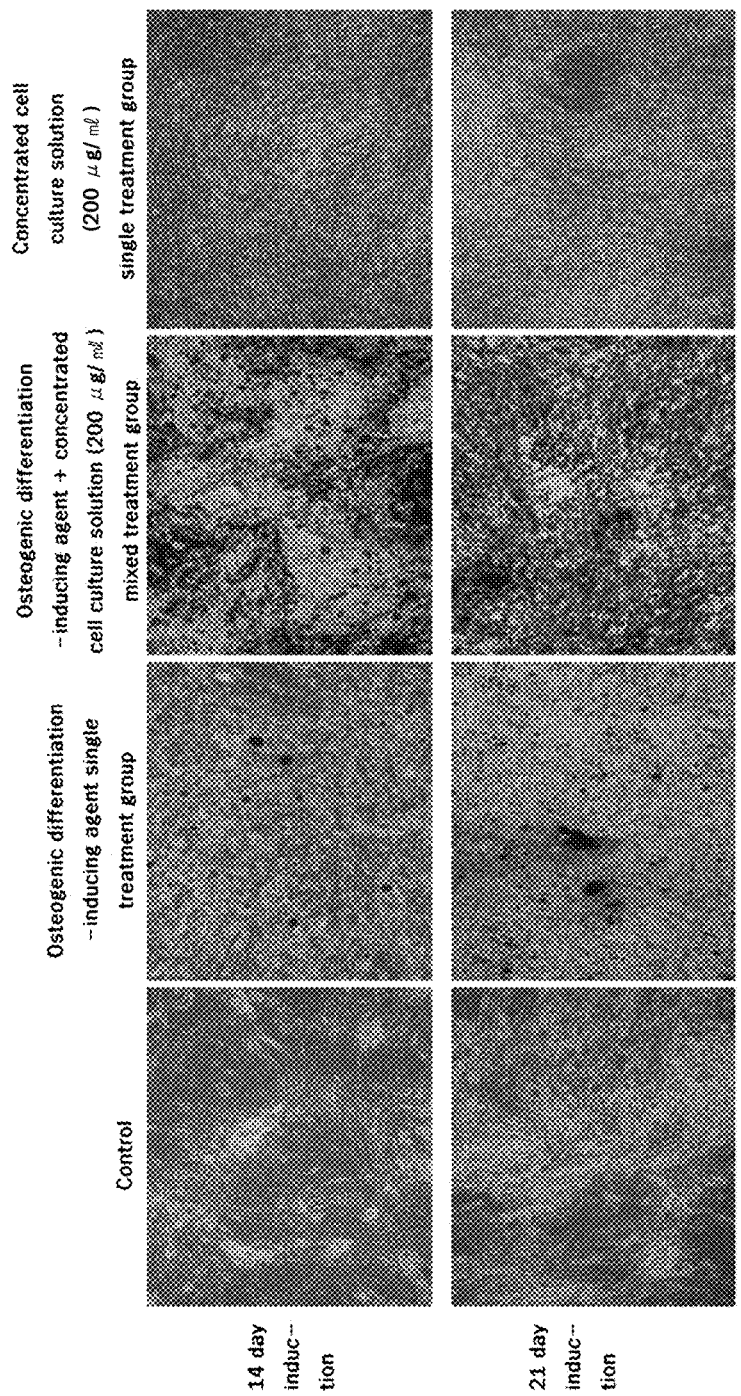
FIG. 6 is a view illustrating the results of confirming the effects of the concentrated progenitor cell culture solution of the present invention according to an exemplary embodiment of the present invention on the promotion of osteogenic differentiation of stem cells with Alizarin Red S.

As illustrated in FIG. 6, it was confirmed that in the case of an experimental group (osteogenic differentiation-inducing agent and concentrated cell culture solution mixed treatment group) compared to a control grown in a bone cell differentiation inducing medium (osteogenic differentiation-inducing agent alone treatment group), differentiation into bone cells was effectively promoted on day 14, and it was confirmed that the osteogenic differentiation was maximized on day 21. However, it was confirmed that differentiation was not induced in a control cultured in a general stem cell culture medium and a control treated with the concentrated culture solution of the present invention alone.

In order to reconfirm whether there was a difference among individuals, an osteogenic differentiation induction experiment was performed on mesenchymal stem cells derived from the adipose tissues of three different persons in the same manner as in Example 4.1 for 14 days. The results are illustrated in FIG. 7.

Figure 7:
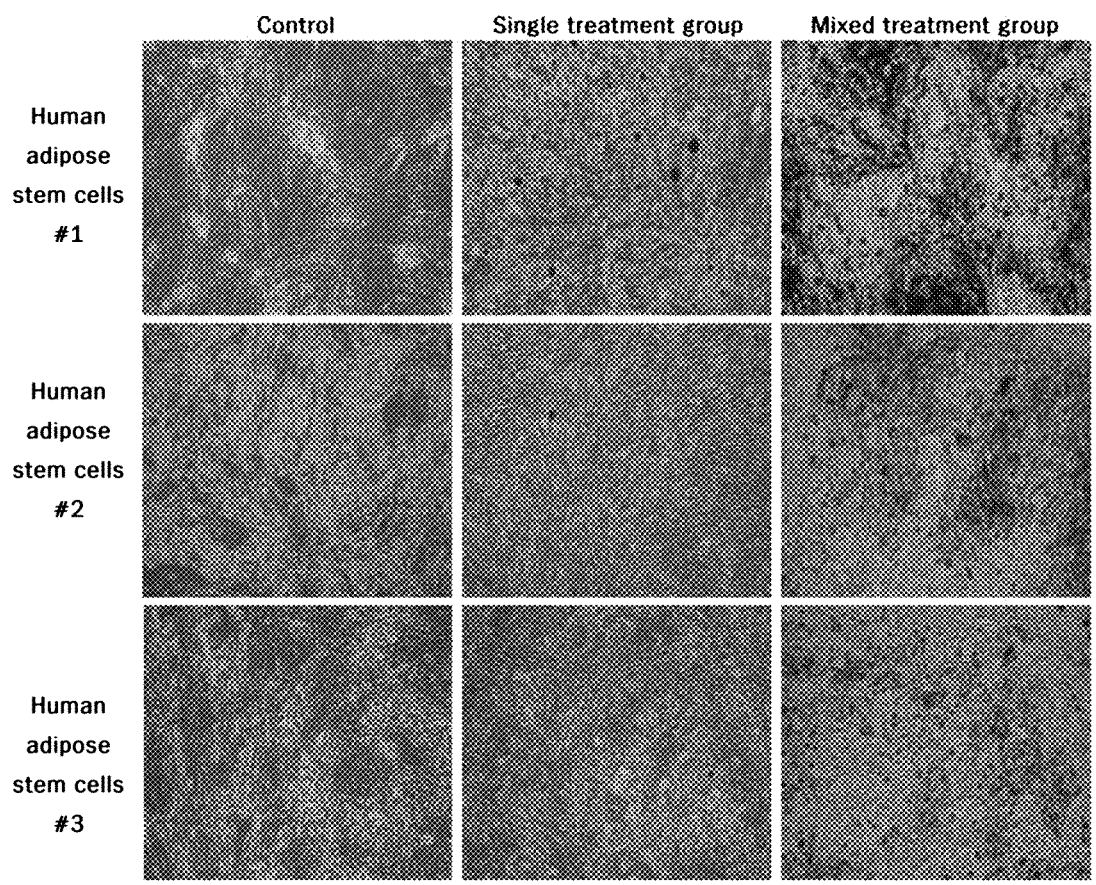
FIG. 7 is a view illustrating the results of confirming the effects of the concentrated progenitor cell culture solution of the present invention according to an exemplary embodiment of the present invention on the promotion of osteogenic differentiation of stem cells with Alizarin Red S.

As illustrated in FIG. 7, it was confirmed that although bone cell differentiation was promoted in the mesenchymal stem cells cultured in the bone cell differentiation inducing medium, there was a difference among individuals and the differentiation efficiency was not high, whereas it was confirmed that in the case of mesenchymal stem cells cultured in the bone cell differentiation inducing medium supplemented with the concentrated culture solution of the present invention, the efficiency and rate of differentiation into bone cells were similarly promoted in all three samples.

In addition, in order to quantify the amount of stained ARS, after the residual water remaining in the container was removed, ARS was eluted by adding 1 ml of a 10% cetylpyridinium chloride (CPC) buffer solution (Sigma) and allowing the resulting mixture to react at room temperature for 30 minutes. 200 µl of the eluted ARS was aliquoted into 96 well plates (SPL), and the absorbance at 550 nm was measured using a microplate reader device (Molecular Devices). The results are illustrated in FIG. 8A.

Figure 8:
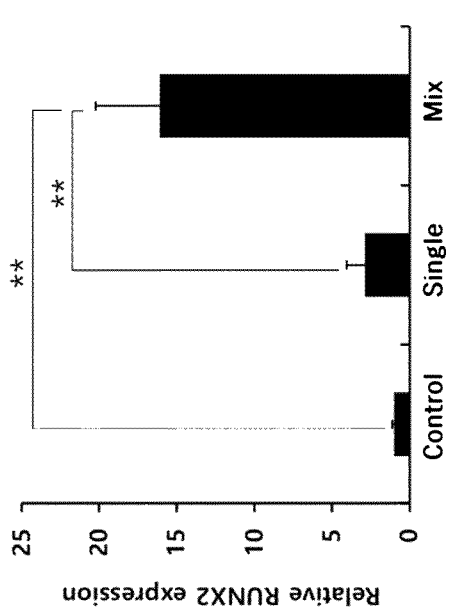
FIG. 8 is a view illustrating the results of quantitatively analyzing the effects of the concentrated progenitor cell culture solution of the present invention according to an exemplary embodiment of the present invention on the promotion of osteogenic differentiation of stem cells, (a) is a view illustrating the quantification results of Alizarin Red S staining, and (b) is a view illustrating the results of confirming the expression levels of the Runx2 gene.
Figure 8:
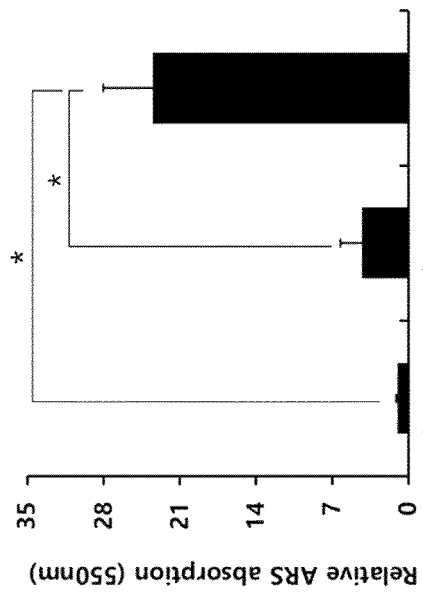
Figure 8:

As illustrated in FIG. 8A, it was confirmed that in the case of stem cells cultured in the bone cell differentiation inducing medium supplemented with the concentrated culture solution of the present invention, differentiation into bone cells was remarkably promoted compared to the controls.

4.3. Confirmation of RUNX2 Gene Expression Level

The expression level of the Runx2 gene in the mesenchymal stem cells whose osteogenic differentiation was induced in the same manner as in Example 4.1 was analyzed using real-time PCR. The Runx2 gene is known to be the most important transcription factor in osteogenic differentiation. Specifically, mRNA was extracted by a phenol-chloroform extraction method using a TRIzol reagent, cDNA was synthesized using a reverse transcription-polymerase chain reaction (RT-PCR), and then real-time PCR was performed using primers specific for Runx2 and the control gene GAPDH gene. Information on the primers used for PCR is shown in the following Table 2. The results of analyzing the relative gene expression level by subjecting PCR products to electrophoresis on an agarose gel are illustrated in FIG. 8B.

TABLE 2

| Gene | SEQ ID NO | Base sequence |
|---|---|---|
| humanGAPDH | 11 | 5'-GAGTCAACGGATTTGGTCGT-3' |
|  | 12 | 5'-TTGATTTTGGAGGGATCTCG-3' |
| humanRUNX2 | 13 | 5'-GACAGCCCCAACTTCCTGT-3' |
|  | 14 | 5'-CCGGAGCTCAGCAGAATAAT-3' |

As illustrated in FIG. 8B, in the case of stem cells cultured in the bone cell differentiation inducing medium supplemented with the concentrated culture solution of the present invention, the expression of the Runx2 gene was remarkably increased compared to the controls, and through this, it was confirmed that differentiation into bone cells were promoted.

Through the results, it could be confirmed that the chick bone and cartilage progenitor cell culture solution could remarkably promote stem cell differentiation.

Example 5: Osteogenic Differentiation Promotion Experiment of Mesenchymal Stem Cells Using Multilayer Graphene Film 5.1. Induction of Differentiation into Bone Cells In order to confirm the effective induction of osteogenic differentiation of human adipose tissue-derived mesenchymal stem cells on a glass substrate coated with a graphene film manufactured in the same manner as in Example 1, specifically, a glass substrate coated with a graphene film having 1, 2, 3, 5, or 7 laminated layers and to confirm the optimal osteogenic differentiation induction environment, after $1 \times 10^5$ cells of mesenchymal stem cells were seeded on a glass substrate coated with a multilayer graphene film having a 24-well culture plate size and an uncoated glass substrate (control), bone cell differentiation was induced when the confluency reached about 90%. Bone cell differentiation was performed by culturing cells in each of the following culture environments for 14 days, and the medium was exchanged once every 3 days. 1) a low glucose DMEM medium (control) supplemented with 10% fetal bovine serum and 1% antibiotic, which is a general stem cell culture medium, without any differentiation inducer on a glass substrate which is not coated with a graphene film, 2) a bone cell differentiation inducing medium (control) on a glass substrate which is not coated with a graphene film, 3) a general stem cell culture medium (a low glucose DMEM medium supplemented with 10% fetal bovine serum and 1% antibiotic) on a glass substrate coated with a graphene film, and 4) a bone cell differentiation inducing medium on a glass substrate coated with a graphene film. As the bone cell differentiation inducing medium, a low glucose DMEM medium supplemented with 0.05 mM ascorbate-2-phosphate, 10 mM β-glycerophosphate, $10^{-7}$ M dexamethasone, 10% fetal bovine serum, and 1% antibiotic was used.

5.2. Confirmation of Alizarin Red S Staining

After stem cell differentiation was induced in the same manner as in Example 5.1, Alizarin Red S staining was performed in the same manner as in Example 4.2. The results are illustrated in FIG. 9.

Figure 9:
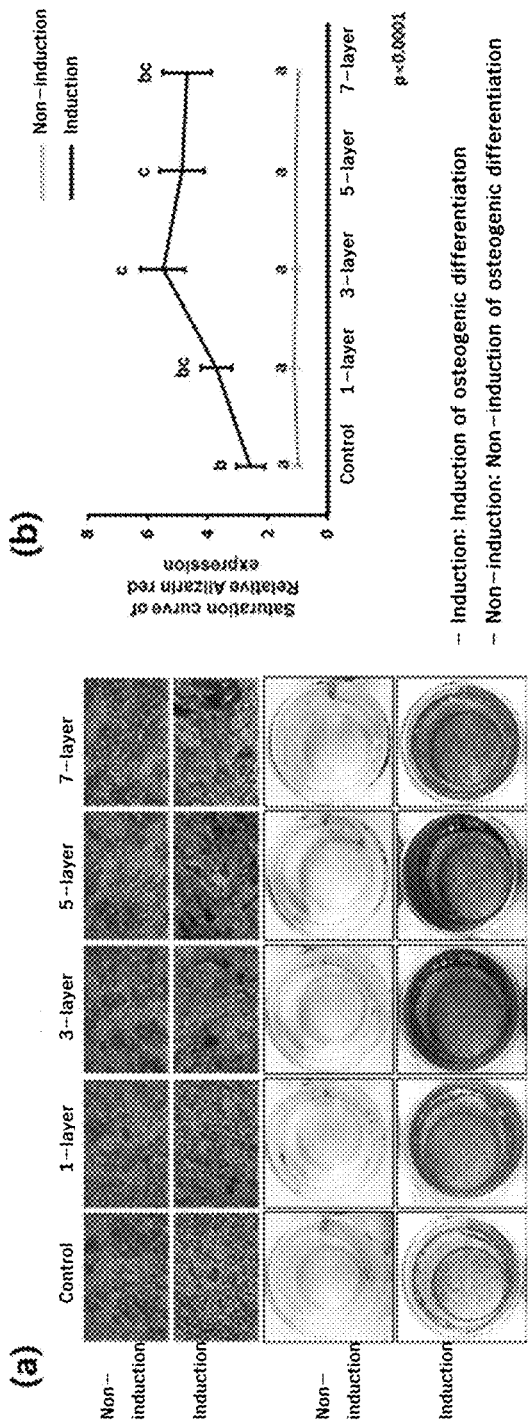
FIG. 9 is a view illustrating the results of confirming the effects of the lamination degree of the graphene according to an exemplary embodiment of the present invention, (a) is a view illustrating the results of photographing the differentiation degree of human adipose-derived mesenchymal stem cells according to a stem cell culture medium or osteocyte-differentiation inducing medium composition according to the lamination degree (1, 3, 5, and 7 layers) of the graphene film, and (b) is a view illustrating a graph quantitatively calculating the osteogenic differentiation degree.

As illustrated in FIG. 9, it was confirmed that osteogenic differentiation was increased on a glass substrate coated with a graphene film compared to a glass substrate (control) which was not coated with graphene, and the differentiation into bone cells was effectively increased in 14 days on the substrate coated with the graphene film laminated in multiple layers compared to the single layer graphene film. Further, it was confirmed that the 3-layer multilayer graphene film was most effective for osteogenic differentiation of stem cells and the differentiation rate into bone cells was not increased any more when using more than 3 laminated layers, and it was confirmed that the differentiation of stem cells was not promoted in the basic culture medium. In order to additionally confirm the effects of the multilayer graphene film on the osteogenic differentiation of stem cells, an osteogenic differentiation experiment was identically performed using the graphene films having 1, 2 and 3 layers. The results are illustrated in FIG. 10.

Figure 10:
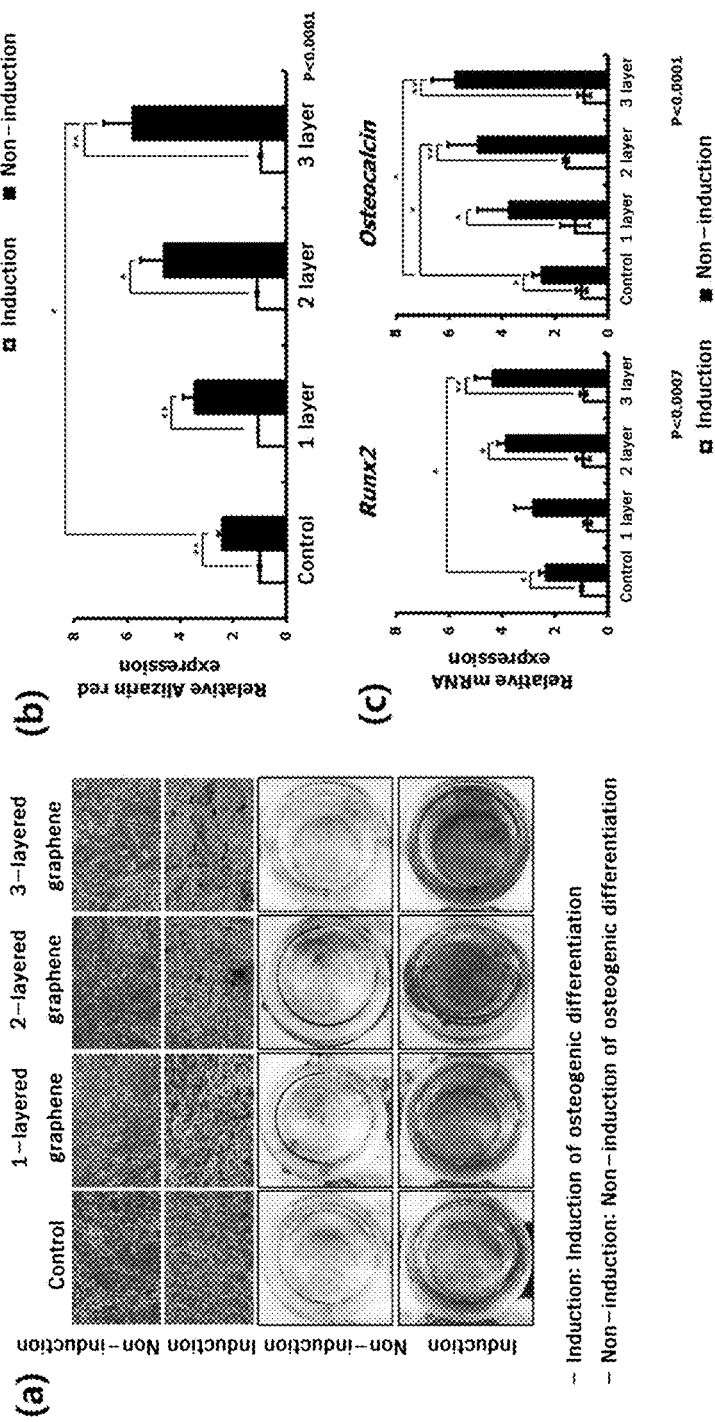
FIG. 10 is a view illustrating the results of confirming the effects of the lamination degree of the graphene according to an exemplary embodiment of the present invention on the osteogenic differentiation of stem cells, (a) is a view illustrating the results of photographing the differentiation degree of mesenchymal stem cells according to the lamination degree (1, 2, and 3 layers) of the graphene film, (b) is a view illustrating a graph quantitatively calculating the osteogenic differentiation degree, and (c) is a view illustrating the results of quantitatively calculating the expression levels of Runx2 and Osteocalcin genes.

As illustrated in FIG. 10, it was confirmed that the osteogenic differentiation of mesenchymal stem cells was significantly promoted most effectively in the 3-layer multilayer graphene film in the same manner as in the experimental results.

Through the results, it could be confirmed that a 2- to 5-layer multilayer graphene film was effective for osteogenic differentiation of stem cells, a 3-layered graphene film is the most effective among them, and the time point of stem cell differentiation could be accurately adjusted using the multilayer graphene film of the present invention.

5.3. Analysis of Expression Levels of RUNX2 and OSTEOCALCIN Genes

In order to accurately analyze the promotion of bone cell differentiation induction in the multilayer graphene film of the present invention, specifically, a glass substrate coated with a 2- or 3-layer multilayer graphene film, the expression levels of Runx2 and Osteocalcin genes in mesenchymal stem cells whose osteogenic differentiation was induced in the same method as in Example 5.1 were analyzed using real-time PCR. Runx2 and Osteocalcin genes are known to be core transcription factors for osteogenic differentiation. Real-time PCR was performed in the same manner as in Example 4.3, and the information on the primers used for PCR is shown in the following Table 3. The results of analyzing the relative gene expression level by subjecting PCR products to electrophoresis on an agarose gel are illustrated in FIG. 10C.

TABLE 3

| Gene | SEQ ID NO | Base sequence |
|------|-----------|---------------|
| humanGAPDH | 11 | 5'-GAGTCAACGGATTTGGTCGT-3' |
| | 12 | 5'-TTGATTTTGGAGGGATCTCG-3' |
| humanRUNX2 | 13 | 5'-GACAGCCCCAACTTCCTGT-3' |
| | 14 | 5'-CCGGAGCTCAGCAGAATAAT-3' |
| human OSTEOCALCIN | 15 | 5'-AGCAAAGGTGCAGCCTTTGT-3' |
| | 16 | 5'-GCGCCTGGGTCTCTTCAT-3' |

As illustrated in FIG. 10C, it was confirmed that the expression of Runx2 and Osteocalcin genes was remarkably increased in the case of mesenchymal stem cells cultured in a differentiation-inducing medium on a glass substrate coated with a multilayer graphene film.

Through the results, it could be confirmed that minute differences in thickness in nm units affected stem cell differentiation, and it was possible to derive a result that the multilayer graphene film, which was particularly laminated in three layers among the multilayer graphene films, quantitatively and significantly promotes osteogenic differentiation of mesenchymal stem cells having multipotency.

Example 6: Confirmation of Promotion of Stem Cell Differentiation of Progenitor Cell Culture Solution and Multilayer Graphene Film 6.1. Induction of Differentiation into Bone Cells In order to confirm the effects of a combination of the progenitor cell culture solution and the multilayer graphene film on the promotion of stem cell differentiation, after $1 \times 10^5$ cells of human adipose tissue-derived mesenchymal stem cells were seeded on a glass substrate coated with a 3-layered graphene film having a 24-well culture plate size, differentiation into bone cells was induced when the confluency reached about 90%. Bone cell differentiation was performed by culturing cells in the following culture environments for 8 or 14 days, and the medium was replaced with a new medium once every 3 days. 1) use of a low glucose DMEM medium supplemented with 10% fetal bovine serum and 1% antibiotic, which is a general cell culture medium, on a glass substrate coated with a 3-layer multilayer graphene film (multilayer graphene alone, control), 2) use of a bone cell differentiation inducing medium on a glass substrate coated with a 3-layer multilayer graphene film (multilayer graphene and differentiation inducer, control), 3) use of a bone cell differentiation inducing medium supplemented with a 100 µg/ml concentrated culture solution on a glass substrate coated with a 3-layer multilayer graphene film (multilayer graphene, differentiation inducer, and concentrated culture solution, experimental group), and as the bone cell differentiation inducing medium, a low glucose DMEM medium supplemented with 0.05 mM ascorbate-2-phosphate, 10 mM β-glycerophosphate, $10^{-7}$ M dexamethasone, 10% fetal bovine serum, and 1% antibiotic was used.

6.2. Confirmation of Alizarin Red S Staining

After osteogenic differentiation of stem cells was induced in the same manner as in Example 6.1, Alizarin Red S staining was performed in the same manner as in Example 4.2. The results are illustrated in FIGS. 11 and 12.

Figure 11:
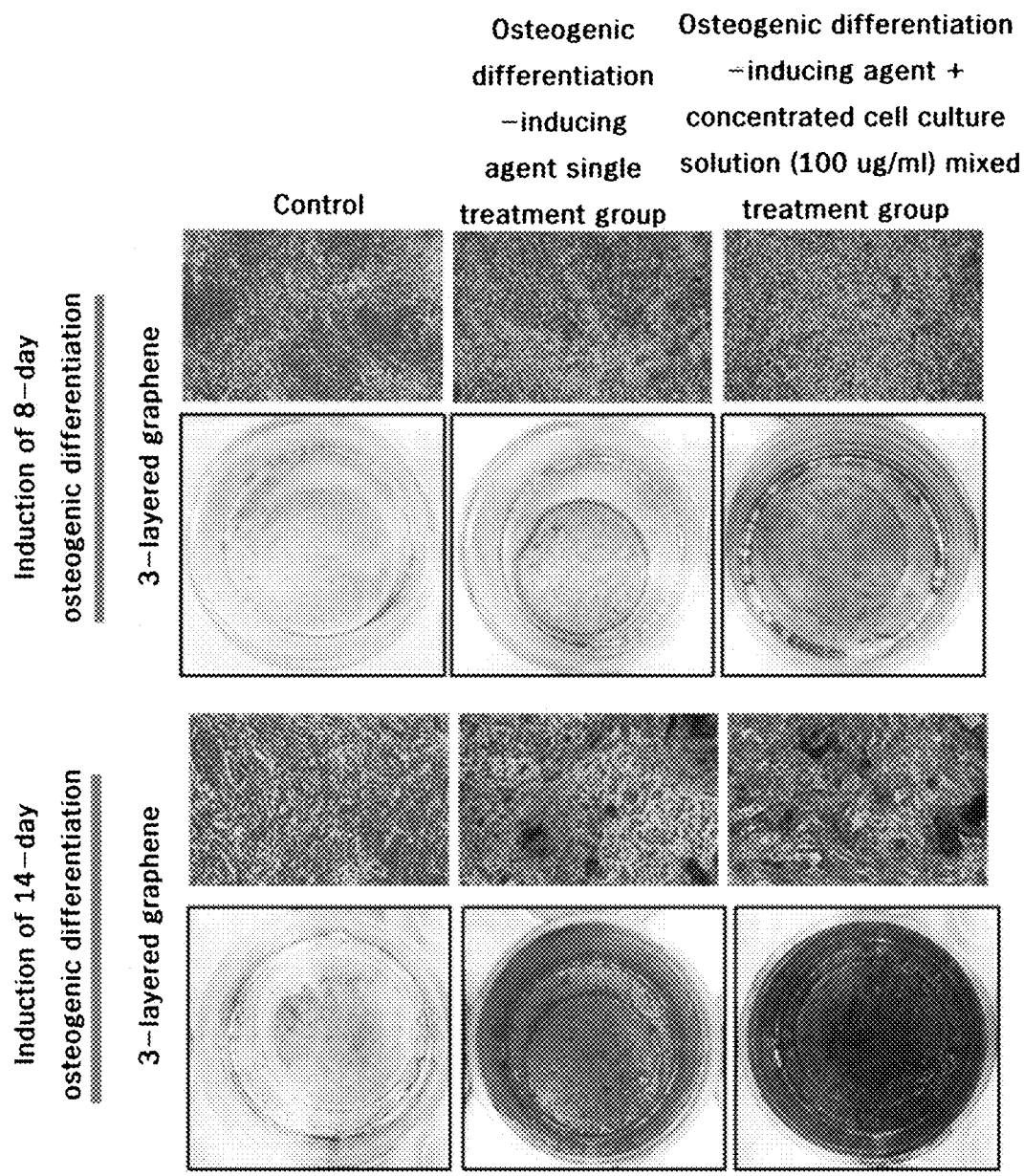
FIG. 11 is a view illustrating the results of confirming the effects of the cell culture solution and the multilayer graphene film according to an exemplary embodiment of the present invention on the ostegenic differentiation of mesenchymal stem cells by Alizarin Red S staining.
Figure 12:
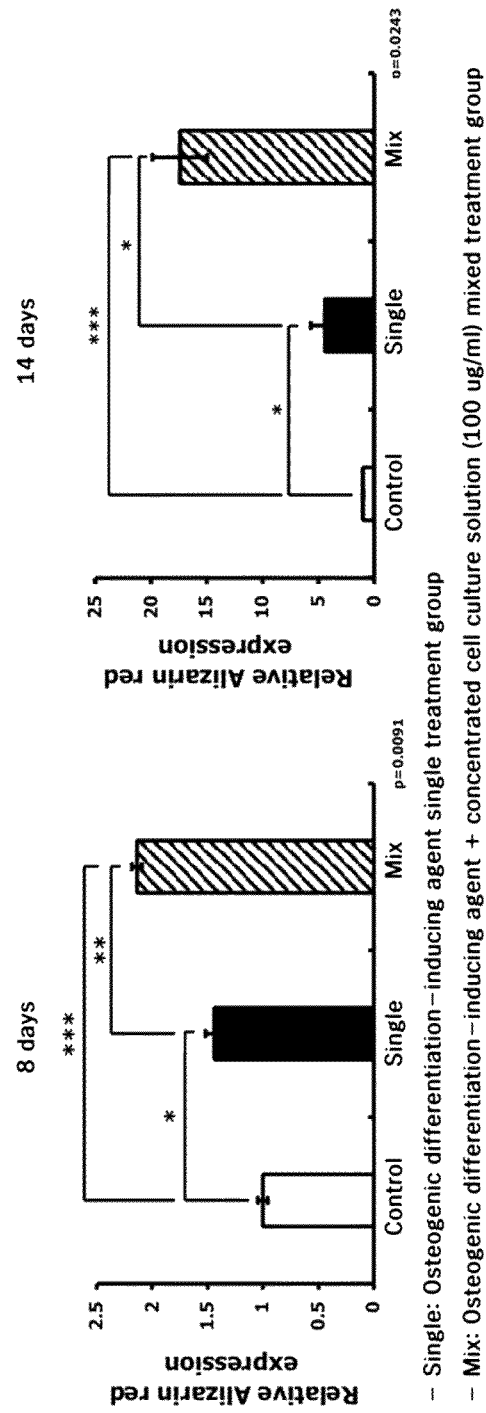
FIG. 12 is a view illustrating a graph showing a quantitative analysis of Alizarin Red S staining according to an exemplary embodiment of the present invention.

As illustrated in FIGS. 11 and 12, it was confirmed that in the experimental group treated with the progenitor cell culture solution of the present invention, the induction of osteogenic differentiation was promoted from day 8 and the differentiation rate was remarkably different on day 14 compared to the control.

6.3. Confirmation of RUNX2 Gene Expression Level

After osteogenic differentiation of stem cells was induced in the same manner as in Example 6.1, real-time PCR was performed in the same manner as in Example 4.3. The results are illustrated in FIG. 13.

Figure 13:
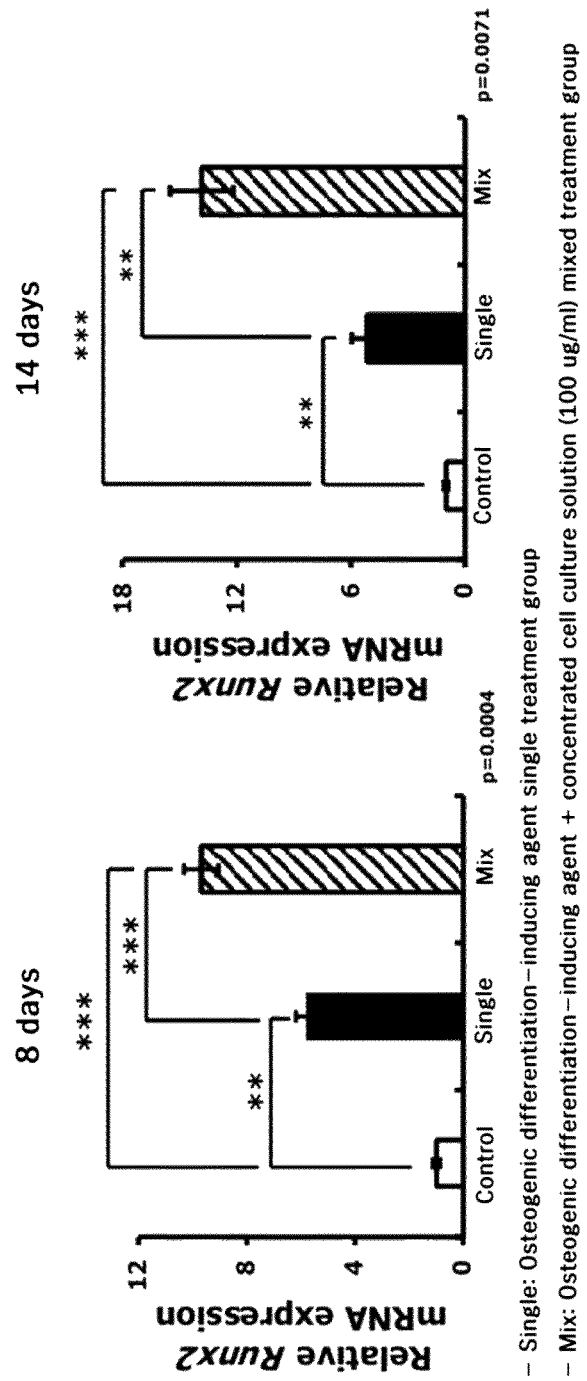
FIG. 13 is a view illustrating the results of confirming the effects of the cell culture solution and the multilayer graphene film according to an exemplary embodiment of the present invention on the ostegenic differentiation of mesenchymal stem cells through the expression levels of the Runx2 gene.

As illustrated in FIG. 13, it was confirmed that when compared to the control coated with the 3-layer multilayer graphene film where osteogenic differentiation was not induced, the expression of the Runx2 gene was significantly increased in mesenchymal stem cells cultured on a substrate coated with a 3-layer multilayer graphene film supplemented with an osteogenic differentiation induced medium, but in the case of mesenchymal stem cells cultured on a substrate coated with a 3-layer multilayer graphene film supplemented with a bone cell differentiation inducing medium supplemented with 100 µg/ml of the concentrated progenitor cell culture solution of the present invention, osteogenic differentiation was further remarkably promoted compared to an experimental group in which the multilayer graphene film was used alone.

Through the results, it was confirmed that coating with the multilayer graphene film effectively promoted osteogenic differentiation of mesenchymal stem cells having multipotency, and effectively improved the differentiation-inducing effect when the number of graphene layers was in a range of 2 to 5. Further, it was confirmed that the differentiation induction was further remarkably improved when the cell culture solution of the progenitor cells was additionally added. Through this, it could be confirmed that the multilayer graphene film coated with the progenitor cell culture solution could be transferred to various substrates such as a glass substrate, a silicon wafer, and a cell culture plate, and could be widely used as a culture support for promoting differentiation of stem cells, and can be used for various treatments using stem cells through the combination of progenitor cell culture solution and multilayer graphene film of the present invention. In particular, it could be confirmed that the multilayer graphene film could be used for the treatment of various bone diseases because the multilayer graphene film could remarkably promote osteogenic differentiation of stem cells.

Although specific parts of the present invention have been described in detail, it is obvious to those skilled in the art that such specific descriptions are only preferred embodiments and the scope of the present invention is not limited thereby. Accordingly, the substantial scope of the present invention will be defined by the appended claims and equivalents thereof.

INDUSTRIAL APPLICABILITY

The composition for promoting stem cell differentiation, comprising a progenitor cell culture solution and a multilayer graphene film according to the present invention has a differentiation efficiency which is 2-fold or higher compared to an existing method of inducing osteoblasts, and can promote the differentiation of stem cells using only a carbon atom, which is harmless to the human body, and a culture solution from which cells of progenitor cells are removed, so that the composition is expected to be widely usable in the treatment of diseases using various stem cells because it is possible to remarkably reduce the occurrence of side effects. In addition, the composition is expected to enable the development of a culture vessel which promotes osteoblast differentiation, a bone chip for bone tissue regeneration, and the like. Therefore, the present invention is expected to be easily applicable to various research fields such as such as medical/biotechnology industry, nanoscience, the microscope industry, the materials industry, agriculture and the fishing industry.

The invention claimed is:

1. A method comprising culturing stem cells in a composition comprising an osteochondroprogenitor cell culture solution and a multilayer graphene film as active ingredients, and thereby promoting the growth and osteogenic differentiation of stem cells,
wherein the multilayer graphene film has 2 to 7 layers formed by lamination of single-layered graphene.

2. The method of claim 1, wherein the culture solution is a culture solution from which cells have been removed after culturing the osteochondroprogenitor cells.

3. The method of claim 1, wherein the stem cells are any one or more selected from the group consisting of embryonic stem cells and adult stem cells.

4. The method of claim 3, wherein the adult stem cells are any one or more selected from the group consisting of mesenchymal stem cells, hematopoietic stem cells, adipose-derived stem cells, and neural stem cells.

5. The method of claim 1, wherein a surface of the multilayer graphene film is coated with the osteochondroprogenitor cell culture solution.

6. The method of claim 1, wherein a surface of the multilayer graphene film is additionally attached with cell adhesion molecules.

7. The method of claim 1, wherein a surface of the multilayer graphene film is patterned using electron beam lithography or photolithography.

8. The method of claim 1, wherein wrinkles are formed on the surface of the multilayer graphene film.

* * * * *